United States Patent [19]

Doyle

[11] Patent Number: 5,328,364

[45] Date of Patent: Jul. 12, 1994

[54] DENTAL CLAMP

[76] Inventor: Walter A. Doyle, 3284 Paris Pike, Lexington, Ky. 40511

[21] Appl. No.: 136,364

[22] Filed: Oct. 15, 1993

[51] Int. Cl.$^5$ .............................................. A61C 3/00
[52] U.S. Cl. .................................................... 433/18
[58] Field of Search ....................... 433/18, 6, 19, 215

[56] References Cited

U.S. PATENT DOCUMENTS

| 4,813,869 | 3/1989 | Gatewood | 433/18 |
| 4,880,380 | 11/1989 | Martz | 433/18 |
| 5,173,048 | 12/1992 | Summer | 433/6 |

Primary Examiner—Cary E. O'Connor
Attorney, Agent, or Firm—Emrich & Dithmar

[57] ABSTRACT

Apparatus for attaching to two or more adjacent teeth maintains the teeth in fixed position relative to one another and permits various orthodontic appliances such as rubber bands, "Herbst" appliances, maxillary expansion appliances, elastics, wires, etc., to be attached. One embodiment includes a pair of spaced, screw-tightened, generally C-shaped clamp members positioned between adjacent teeth which are connected by means of one or more elongated side arms disposed adjacent lateral portions of the teeth being clamped together. A screw in each C-clamp member permits secure attachment between adjacent teeth, with the side arm inserted through an aperture in each C-clamp member and secured by crimping permitting the length of the side arm to be fixed as required. The side arm, or arms, may be rigid or flexible to accommodate various sizes and alignments of the clamped teeth. Appliances may be attached to the tightening screw or to the side arms which also function to prevent the C-clamp member from separating the teeth. Another embodiment employs a single C-clamp member with a pair of side arms, with the C-clamp member attached to an intermediate portion of each side arm. Respective ends of each side arm include a tooth engaging element for maintaining the teeth in fixed relation. The screw attachment prevents removal by the user and eliminates the need for "bonding" and band attachment arrangements.

20 Claims, 2 Drawing Sheets

DENTAL CLAMP

FIELD OF THE INVENTION

This invention relates generally to orthodontic apparatus and is particularly directed to apparatus for attaching to two or more adjacent teeth for maintaining the teeth in fixed position relative to one another.

BACKGROUND OF THE INVENTION

Abnormally positioned teeth are not only unattractive, but they are generally difficult to clean, resulting in decay and damage to the teeth and gums. Great advances in orthodontics have allowed for the movement of teeth by applying a constant pressure so as to position the teeth in an aligned, properly spaced array within one's mouth. Movement of teeth is accomplished by various orthodontic appliances which are generally referred to by the layman as "braces". The orthodontic appliance is attached to the teeth by means of bands disposed about the teeth or by means of bonding the appliance to the teeth using a conventional adhesive. Bands are difficult to tightly position about one's teeth, and bonding gives rise to the potential for decay of a tooth in the vicinity where the appliance is attached. In addition, an appliance bonded to a tooth is difficult to remove, with some of the adhesive frequently remaining affixed to the tooth after appliance removal. Most available orthodontic appliances are also not readily adapted for attachment to other appliances such as rubber bands, "Herbst" appliances, and maxillary expansion appliances and frequently make the installation of such appliances quite difficult.

The present invention addresses the aforementioned limitations of the prior art by providing a dental clamp device which is easily installed and removed by a dentist and which is essentially patient-proof in terms of removal and which eliminates the need for bonding or bands while maintaining adjacent teeth in fixed relative position and orientation.

OBJECTS AND SUMMARY OF THE INVENTION

Accordingly, it is an object of the present invention to provide apparatus for attaching to two or more adjacent teeth for maintaining the teeth in fixed relative position and orientation.

It is another object of the present invention to provide an orthodontic apparatus which facilitates the attachment of various orthodontic appliances such as rubber bands, "Herbst" appliances, maxillary expansion appliances, elastics, wires, etc., without the need for "bonding" the appliance or placing bands on teeth.

Yet another object of the present invention is to provide an orthodontic dental clamp which can be easily applied to a patient by the doctor and which cannot be removed by the patient and thus eliminates the need of cooperation by the patient.

A further object of the present invention is to provide a dental clamp which can be easily modified as well as adjusted for size for various uses such as the retention of a rubber dam, separation of teeth, attachment of various intra-oral research devices, medication release, precise control of the movement and direction of growth of adjacent teeth, etc.

These objects of the present invention are achieved and the disadvantages of the prior art are eliminated by apparatus for maintaining first and second teeth fixed relative to one another, the apparatus comprising: first and second clamp members respectively engaging distal, opposed, end portions of the first and second teeth, wherein each clamp member includes first and second elongated arms coupled together in a telescoping manner and spaced, opposed tooth engaging elements for engaging proximal, opposed portions of the first and second teeth, each of the clamp members further including a tightening mechanism for drawing the first and second elongated arms together and positioning the engaging elements in tight-fitting engagement with the first and second teeth; at least one side arm disposed adjacent a first lateral portion of the first and second teeth; and a coupling arrangement for securely attaching the at least one side arm to the first and second clamp members and maintaining the clamp members in fixed relation, wherein the distance between the first and second clamp members may be fixed in accordance with the size and shape of the first and second teeth.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various Figures, in which:

DETAILED DESCRIPTION OF THE PREFERRED EMBODIMENTS

Figure 1:
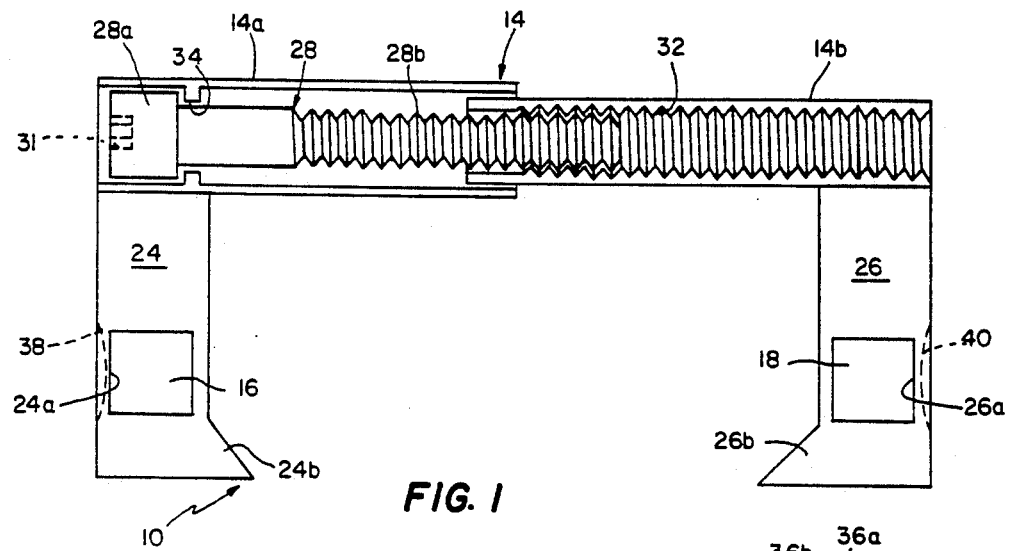
FIG. 1 is a side elevation view shown partially cut away of a dental clamp in accordance with the present invention.
Figure 1A:
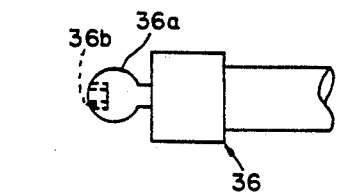
FIG. 1a is a partial side elevation view of a threaded plug for use with the dental clamp of FIG. 1.
Figure 2:
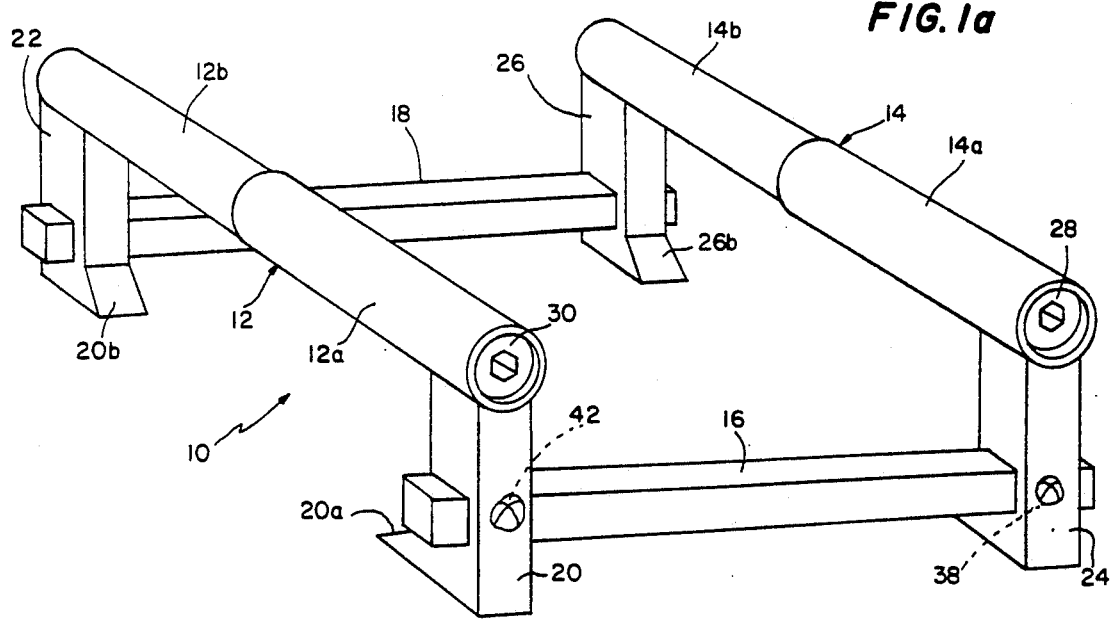
FIG. 2 is a perspective view of the dental clamp shown in FIG. 1.

Referring to FIG. 1, there is shown partially in phantom an elevation view of a dental clamp 10 in accordance with the present invention. FIG. 2 is a perspective view of the dental clamp 10 shown in FIG. 1.

Dental clamp 10 includes first and second elongated, generally linear clamp members 12 and 14. First and second clamp members 12, 14 are aligned generally parallel. The first clamp member 12 includes first and second telescoping, elongated arms 12a and 12b. Similarly, the second clamp member 14 includes first and second telescoping arms 14a and 14b. Second telescoping arms 12b and 14b are each adapted for sliding positioning within and along the length of first telescoping arms 12a and 14a, respectively. Attached to distal ends of the first telescoping arms 12a and 14a are first struts 20 and 24, respectively. Attached to respective distal ends of the second telescoping arms 12b and 14b are second struts 22 and 26. Coupled to and extending between the pair of first struts 20 and 24 is a first side arm 16. Similarly, coupled to and extending between the pair of second struts 22 and 26 is a second side arm 18. Each of the four struts includes an aperture therein through which a respective one of the side arms is inserted. Thus, as shown in the elevation view of FIG. 1, the first side arm 16 is disposed within an aperture 24a in strut 24. Similarly, the second side arm 18 is inserted through an aperture 26a within strut 26. Although apertures 24a and 26a in struts 24 and 26 and the first and second side arms 16 and 18 are shown with a generally square cross-section, the present invention is not limited to this shape as the side arms may have virtually any cross-sectional shape. Side arms 16, 18 are securely maintained within each of the struts by crimping an adjacent portion of the strut into intimate contact with the side arm. Thus, a first crimp 38 is provided in strut 24 and a second crimp 42 is provided in strut 20 for fixedly attaching side arm 16 to these two struts. Similarly, portions of struts 22 and 26 disposed adjacent the second side arm 18 are crimped inwardly toward the side arm to securely affix the side arm to these struts. Thus, as shown in FIG. 1, strut 26 is provided with an inwardly crimped portion 40 (shown in dotted-line form) for securely engaging side arm 18 in a fixed manner.

The length of each of the first and second clamp members 12 and 14 is adjustable as follows. As shown for the case of the second clamp member 14 in FIG. 1, second telescoping arm 14b is inserted within the larger first telescoping arm 14a. Second telescoping arm 14b is provided with an inner threaded portion 32 along the length thereof. Inserted in the open end of the first telescoping arm 14a of the second clamp member 14 is an elongated, linear threaded plug 28. Threaded plug 28 includes a first keying end portion 28a and a second threaded end portion 28b. Threaded end 28b of plug 28 is adapted for insertion within the second telescoping arm 14b for engaging the internal threads 32 therein. First keying end 28a of threaded plug 28 is positioned in contact with an inner stop 34 within the first telescoping arm 14a to maintain threaded plug in position within the first clamp member 14. Threaded plug 28 is freely rotatable within the first telescoping arm 14a such as by engaging a hexagonal end slot, or recess, 31 in the end of the plug by conventional means such as an Allen wrench (not shown for simplicity). Rotation of threaded plug 28 within the second telescoping arm 14b in a first direction draws the second telescoping arm into the first telescoping arm 14a for shortening the length of the second clamp member 14 and displacing the first and second struts 24 and 26 toward each other. Similarly, rotation of first threaded plug 28 in a second, opposed direction results in movement of the second telescoping arm 14b out of the first telescoping arm 14a and increased separation between the first and second struts 24, 26. In this manner, the first and second struts 24, 26, which are positioned in contact with opposed lateral portions of adjacent teeth as described below may be moved toward or away from each other as determined by the width of the teeth. A second threaded plug 30 disposed in the first clamp member 12 provides for telescoping movement between the first and second arms 12a and 12b and relative displacement between the first and second struts 20, 22. By adjusting the spacing between first and second pairs of struts 20, 22 and 24, 26, the spacing between the first and second side arms 16, 18 may be adjusted in accordance with the width of the teeth to which the dental clamp 10 is affixed. In this manner, the first and second side arms 16, 18 may be displaced toward each other so as to be positioned adjacent respective, opposed lateral portions of adjacent teeth as described below. With the first and second side arms 16, 18 engaging or positioned in closely spaced relation to respective opposed, lateral portions of adjacent teeth, tapered inserts on the distal end of each of the aforementioned struts are positioned in contact with opposed, lateral portions of the teeth for securely attaching the dental clamp 10 to these teeth as described below. FIGS. 1 and 2 show the four struts 20, 22, 24 and 26 as respectively including the aforementioned distal tapered end inserts 20a, 20b, 24b and 26b, respectively. Each of these tapered end inserts is adapted for positioning between and engaging adjacent teeth for facilitating tight attachment of the dental clamp 10 to the adjacent teeth as described below. The first and second side arms 16, 18 may be either rigid or flexible to allow the side arms to assume the lateral contour of the clamped teeth and to accommodate a range of widths of the teeth.

FIG. 1 further shows a partial elevation view of another embodiment of a threaded plug 36 for insertion in the first telescoping arm 14a of the second clamp member 14. Threaded plug 36 includes an end projection 36a having an end slot 36b which may be either hexagonal to accommodate an Allen wrench or linear to accommodate a flathead screwdriver for rotationally displacing the threaded plug in adjusting the length of the second clamp member 14 as described above. End projection 36a is adapted for receiving various orthodontic attachments such as rubber bands, "Herbst" appliances, maxillary expansion appliances, etc. The end projection 36a of threaded plug 36 greatly facilitates the attachment of such appliances without modification of the dental clamp 10 or requiring the use of additional attachments.

Figure 3:
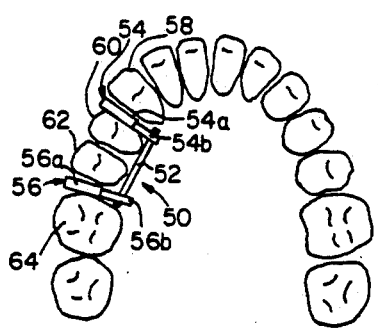
FIG. 3 is a plan view of a set of teeth illustrating the manner in which the dental clamp of the present invention is attached to adjacent teeth.

Referring to FIG. 3, there is shown a plan view of a set of teeth to which is attached a dental clamp 50 in accordance with another embodiment of the present invention. The set of teeth shown in FIG. 3 includes first, second, third and fourth teeth 58, 60, 62 and 64. Dental clamp 50 extends between adjacent teeth 60 and 62 and includes first and second clamp members 54 and 56. As previously described, the first clamp member 54 includes first and second telescoping arms 54a and 54b and the second clamp member 56 includes first and second telescoping arms 56a and 56b. The first and second clamp members 54, 56 are respectively positioned intermediate the first and second teeth 58, 60 and the third and fourth teeth 60 and 64. The first and second clamp members 54, 56 are positioned adjacent distal (or outer) ends of the aforementioned teeth and each includes a respective strut disposed adjacent the inner surfaces of the teeth which extend into the plan of the paper and thus are not shown in the Figure. The first and second clamp members 54, 56 are coupled together by means of a side arm 52 inserted through respective apertures in the aforementioned struts and attached thereto by crimping as previously described. Outer, or distal, ends of each of the first and second clamping members 54, 56 also include respective struts extending into the plane of the paper which also are not shown for simplicity. Each of the aforementioned struts include a respective tapered end insert for engaging proximal portions of adjacent teeth when the first and second clamp members 54, 56 are tightened. In the embodiment shown in FIG. 3, it should be noted that the dental clamp includes only a single side arm 52 which is located adjacent inner surfaces of the teeth being clamped together.

Figure 4:
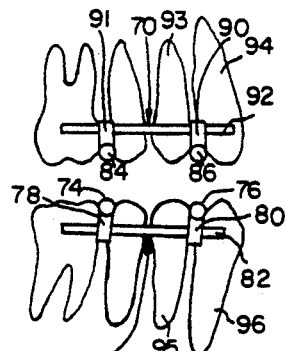
FIG. 4 is a side elevation view of a partial set of upper and lower teeth showing a dental clamp attached to each of the upper and lower sets of teeth in accordance with the present invention.
Figure 5:
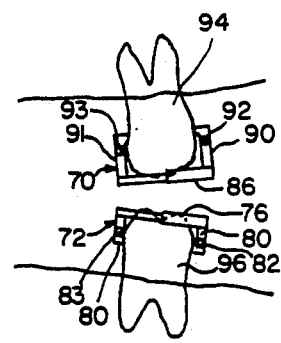
FIG. 5 is an elevation view illustrating additional details of the manner in which the dental clamps shown in FIG. 4 are attached to adjacent teeth.

Referring to FIG. 4, there is shown a side elevation view of upper and lower dental clamps 70 and 72 in position on respective upper and lower sets of teeth. A sectional view of the upper and lower dental clamps 70, 72 taken along a site line between first and second upper teeth 93 and 94 and first and second lower teeth 95 and 96 in a direction toward upper and lower teeth 94 and 96 is shown in FIG. 5. Lower dental clamp 72 includes first and second telescoping clamp members 74 and 76 respectively including first and second pairs of struts 78 and 80. Securely attached to the first and second pairs of struts 78, 80 such as by crimping, as previously described, are first and second side arms 82 and 83. Similarly, upper dental clamp 70 includes first and second telescoping clamp members 84 and 86 and first and second side arms 92 and 93 attached to the strut portions of these clamp members. From these Figures, it can be seen that the telescoping clamp members 74, 76 of the lower dental clamp 72 and the clamp members 80, 86 of the upper dental clamp 70 are disposed adjacent distal ends of adjacent teeth, while the tapered ends of the struts 78, 80 and 90, 91 of the lower and upper dental clamps engage proximal portions of adjacent teeth. The tapered tooth engaging attachments disposed on the ends of the struts thus function to maintain the dental clamp securely in position on the teeth and can also be used to maintain a desired spacing between adjacent teeth. The telescoping clamp members also provide for secure attachment of the dental clamp to the teeth, while inter-tooth spacing is maintained by the lengths of the side arms between the two clamp members.

Figure 6:
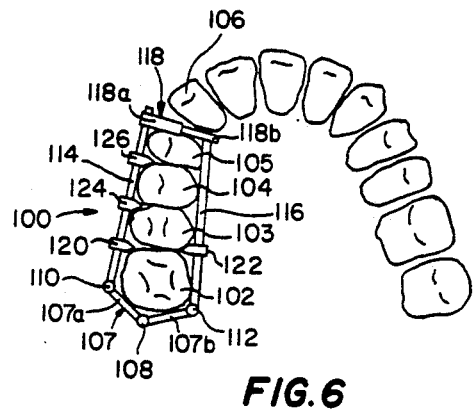
FIG. 6 is a plan view of a set of teeth to which is attached a dental clamp in accordance with another embodiment of the present invention.
Figure 6A:
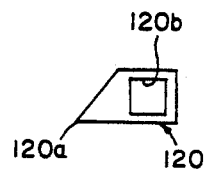
FIG. 6a is an end-on view of a positioning attachment employed in the dental clamp of FIG. 6.

Referring to FIG. 6, there is shown another embodiment of a dental clamp 100 attached to a set of teeth including first, second, third and fourth teeth 102–105. Clamping device 100 includes a first hinged clamp member 107 and a second telescoping clamp member 118. The first hinged clamp member 107 includes first and second pivoting arms 107a and 107b coupled together by means of a center hinge 108 which may be in the form of a pivot pin. First and second end hinges 110 and 112 respectively couple the first and second pivoting arms 107a and 107b to first and second side arms 114 and 116. Center hinge 108 and the first and second end hinges 110, 112 allow the first clamp member 107 to generally conform to and engage lateral portions of the first tooth 102. The second telescoping clamp member 118 is disposed intermediate the fourth tooth 105 and a fifth tooth 106. Telescoping clamp member 118 includes first and second telescoping arms 118a and 118b which allow the length of the clamp member 118 to be adjusted as determined by the width of the first through fourth teeth 102–105. Tightening of the telescoping clamp member 118 draws the first and second side arms 114, 116 toward the lateral surfaces of aligned teeth 102–105. Disposed in a spaced manner along the first side arm 114 are first, second and third positioning attachments 120, 124 and 126. A fourth positioning attachment 122 is disposed on the second side arm 116. Each of these positioning attachments is securely attached to its respective side arm such as by crimping as previously described. Telescoping clamp member 118 is also attached to side arms 114 and 116 in this manner. As shown in the Figure, positioning attachments 120 and 122 are positioned intermediate the first and second teeth 102, 103. Positioning attachments 124 and 126 are respectively positioned between the second and third teeth 103, 104 and the third and fourth teeth 104, 105. Each of the positioning attachments has a tapered distal end. As the second telescoping clamp member 118 is tightened, each of the positioning attachments is brought into engagement with outer lateral portions of adjacent teeth for maintaining the teeth in fixed relative position and orientation. Each of the positioning attachments may be attached directly to a respective one of the side arms or may be extended from a side arm by means of one of the aforementioned struts which are not shown in FIG. 6 for simplicity.

Shown in the right-hand portion of FIG. 6 are details of one of the positioning attachments 120 which is representative of all of the above-described positioning attachments. Positioning attachment 120 includes a generally rectangular aperture 120b through which a side arm is inserted for attaching the positioning attachment to the side arm by crimping. The distal end of positioning attachment 120 is tapered to a relatively sharp point to allow the angled surfaces forming the taper to engage an adjacent tooth and maintain the tooth securely in fixed position.

Figure 7:
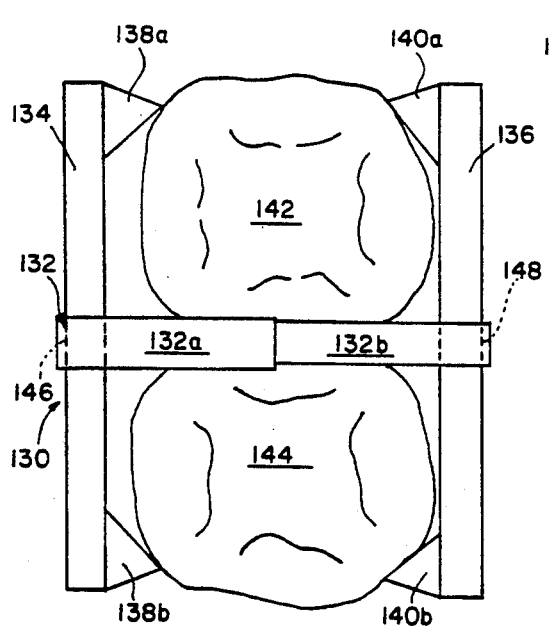
FIG. 7 is a plan view of a pair of teeth to which yet another embodiment of a dental clamp in accordance with the present invention is attached.

Referring to FIG. 7, there is shown another embodiment of a dental clamp 130 in accordance with the present invention. Dental clamp 130 includes a single center clamp member 132 and first and second side arms 134 and 136. Center clamp member 132 includes first and second telescoping arms 132a and 132b as in the previously described embodiments. Extending from respective ends of the center clamp member 132 are first and second struts 146 and 148 shown in the Figure in dotted-line form. Inserted through respective apertures in struts 146 and 148 and securely attached thereto such as by crimping are first and second side arms 134 and 136. First side arm 134 includes first and second inwardly directed tapered end attachments 138a and 138b. Similarly, second side arm 136 includes first and second inwardly directed tapered end attachments 140a and 140b. With the center clamp member 132 positioned intermediate first and second teeth 142 and 144 and in close proximity to or in contact with adjacent facing portions of these two teeth, the first and second side arms 134, 136 are positioned on respective sides of the teeth as shown in the Figure. Tightening of the center clamp member 132 draws the first and second side arms 134, 136 toward each other causing their respective end attachments to engage lateral portions of the first and second teeth 142, 144. As the side arms 134, 136 are further drawn together, the tapered portions of the end attachments 138a, 138b and 140a, 140b urge teeth 142 and 144 together and maintain them securely in fixed relative position.

Figure 8:
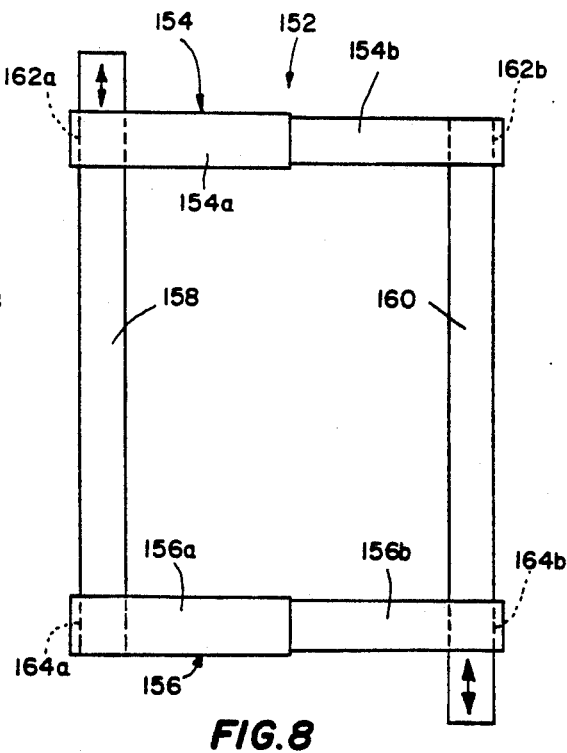
FIG. 8 is a plan view of yet another embodiment of a dental clamp in accordance with the present invention comprised of two identical clamp members.

Referring to FIG. 8, there is shown another embodiment of a dental clamp 152 in accordance with the present invention. Dental clamp 152 includes first and second clamp members 154 and 156. The first clamp member 154 includes first and second telescoping arms 154a and 154b, and the second clamp member 156 also includes first and second telescoping arms 156a and 156b. Attached to respective ends of the first clamp member 154 are first and second struts 162a and 162b (shown in dotted line form). Similarly, attached to respective ends of the second clamp member 156 are first and second struts 164a and 164b (also shown in dotted line form). Strut 164a is fixedly attached to one end of a first side arm 158, while strut 162b is fixedly attached to one end of a second side arm 160. The first side arm 158 is inserted through an aperture within strut 162a, while the second side arm 160 is inserted through an aperture in strut 164b. The first side arm 158 is thus movable with respect to the first clamp member 154, while the second side arm 160 is movable relative to the second clamp member 156. The two side arms 158, 160 may be moved either toward or away from each other by telescoping adjustment of the first and second clamp members 154, 156 in accordance with the width of the teeth. Similarly, the first and second clamp members 154, 156 may be moved toward or away from each other by sliding movement of the side arms within the struts. The separation distance between the clamp members is determined by the size of and spacing between the teeth to be clamped. One of the advantages of the embodiment of the dental clamp 152 shown in FIG. 8 is that it is comprised of two identical structures, one including the combination of the first clamp member 154, its strut 162b and the second side arm 160, while the second structure includes the combination of the second clamp member 156, its strut 164a and the first side arm 158.

There has thus been shown a dental clamp for secure attachment to two or more adjacent teeth for maintaining the teeth in fixed position relative to one another. The inventive dental clamp facilitates the attachment of various orthodontic appliances to the thus clamped teeth. The dental clamp is easily installed by a doctor, yet is patient-proof in terms of its removal. Various adjustable features allow the clamp to be used with a wide range of tooth dimensions and configurations in an arrangement which eliminates the need for "bonding" and band attachments. The dental clamp as described is preferably comprised of metal which can be covered with plastic for fabrication of various appliances, affording a "fixed-removable appliance".

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. Apparatus for maintaining first and second teeth fixed relative to one another, said apparatus comprising: first and second clamp members respectively engaging distal, opposed, end portions of said first and second teeth, wherein each clamp member includes first and second elongated arms coupled together in a telescoping manner and spaced, opposed teeth engaging elements for engaging proximal, opposed portions of said first and second teeth, each of said clamp members further including tightening means for drawing said first and second elongated arms together and positioning said engaging elements in tight-fitting engagement with said first and second teeth;

at least one side arm disposed adjacent a first lateral portion of said first and second teeth; and coupling means for securely attaching said at least one side arm to said first and second clamp members and maintaining said clamp members in fixed relation, wherein the distance between said first and second clamp members may be fixed in accordance with the size and shape of said first and second teeth.

2. The apparatus of claim 1 wherein each of said first and second elongated arms has a generally circular cross-section, and wherein said second elongated arm is disposed within said first elongated arm and is adapted for sliding displacement therein.

3. The apparatus of claim 2 wherein said tightening means includes an inner threaded portion in said second elongated arm and a threaded member disposed in said first elongated arm and engaging said inner threaded portion of said second elongated arm.

4. The apparatus of claim 3 wherein said first elongated arm includes an open end portion adapted to receive said threaded member and stop means disposed within said open end portion for engaging and maintaining said threaded member in position within said first elongated arm.

5. The apparatus of claim 4 wherein said threaded member includes retaining means for attachment to an orthodontic appliance.

6. The apparatus of claim 1 wherein each of said first and second clamp members further includes a respective strut, and wherein each strut couples a teeth engaging element to an elongated arm.

7. The apparatus of claim 6 wherein each of said struts includes a respective aperture for receiving said side arm, and wherein said coupling means includes respective crimped portions on each of said struts for engaging said side arm.

8. The apparatus of claim 7 wherein each of said struts further includes a first proximal end attached to one of said elongated arms and a second distal end having a projection thereon for engaging a proximal, lateral portion of a tooth.

9. The apparatus of claim 8 wherein said projection is tapered having a pointed distal end.

10. The apparatus of claim 1 further comprising a plurality of positioning attachments disposed in a spaced manner along said side arm and positioned intermediate and engaging adjacent teeth.

11. The apparatus of claim 10 further comprising means for adjusting the spacing between said plurality of positioning attachments along said side arm in accordance with the size and spacing between the teeth.

12. The apparatus of claim 1 further comprising first and second side arms coupled to said first and second clamp members and disposed adjacent respective lateral portions of said first and second teeth.

13. The apparatus of claim 12 wherein each of said first and second clamp members further includes first and second struts respectively coupled to said first and second side arms.

14. The apparatus of claim 13 wherein each of said first and second struts includes a respective aperture for receiving one of said side arms, and wherein said coupling means includes crimped portions on each of said struts for engaging a respective side arm.

15. The apparatus of claim 14 wherein each of said first and second struts further includes a first end attached to one of said elongated arms and a second distal end having a projection thereon for engaging a proximal, lateral portion of a tooth.

16. The apparatus of claim 12 wherein at least one of said first and second clamp members includes flexible means for allowing said clamp member to conform to a lateral surface of one or more of the teeth.

17. The apparatus of claim 16 further comprising a plurality of struts disposed in a spaced manner along said side arms and positioned intermediate and engaging adjacent teeth.

18. The apparatus of claim 12 wherein said first clamp member and said first side arm are fixedly attached to each other forming a first integral clamp assembly and said second clamp member and said second side arm are fixedly attached to each other to form a second integral clamp assembly, and wherein said first and second clamp assemblies are essentially identical in size and configuration.

19. The apparatus of claim 1 wherein said at least one side arm is flexible for allowing said side arm to conform to a lateral surface of one or more of the teeth.

20. Apparatus for maintaining adjacent first and second teeth fixed relative to one another, said apparatus comprising:

a clamp member disposed intermediate said teeth and including first and second elongated arms coupled together in a telescoping manner;

first and second side arms disposed adjacent respective opposed lateral portions of said teeth, wherein each of said side arms is coupled to a respective end of said clamp member and includes first and second spaced teeth engaging members for engaging lateral portions of said first and second teeth, respectively; and tightening means attached to said clamp member for drawing said first and second elongated arms and said first and second side arms together, wherein said teeth engaging members maintain said first and second teeth in fixed position relative to one another.

* * * * *